(12) United States Patent
Thorpe (10) Patent No.: US 9,016,968 B2
(45) Date of Patent: Apr. 28, 2015

(54) COSMETIC DEVICE WITH THERMAL STORAGE TIP

(71) Applicant: HCT Packaging, Inc., Santa Monica, CA (US)

(72) Inventor: Timothy Thorpe, Santa Monica, CA (US)

(73) Assignee: HCT Asia Ltd., Hong Kong (HK)

( * ) Notice: Subject to any disclaimer, the term of this patent is extended or adjusted under 35 U.S.C. 154(b) by 0 days.

(21) Appl. No.: 13/656,993

(22) Filed: Oct. 22, 2012

(65) Prior Publication Data

US 2013/0108349 A1   May 2, 2013

Related U.S. Application Data

(63) Continuation of application No. 13/022,193, filed on Feb. 7, 2011, now Pat. No. 8,292,535, which is a continuation of application No. 11/747,078, filed on May 10, 2007, now Pat. No. 7,883,287.

(51) Int. Cl.
| | |
|---|---|
| *B05C 11/00* | (2006.01) |
| *A45D 40/26* | (2006.01) |
| *A45D 34/04* | (2006.01) |
| *A61M 35/00* | (2006.01) |
| *B05B 11/00* | (2006.01) |
| *B65D 83/14* | (2006.01) |

(52) U.S. Cl.
CPC ............... *A45D 40/26* (2013.01); *A45D 34/04* (2013.01); *A45D 2200/051* (2013.01); *A45D 2200/055* (2013.01); *A45D 2200/056* (2013.01); *A45D 2200/152* (2013.01); *A45D 2200/155* (2013.01); *A61M 35/003* (2013.01); *B05B 11/30* (2013.01); *B65D 83/14* (2013.01)

(58) Field of Classification Search
USPC ......................................... 401/261–266, 6, 9
See application file for complete search history.

(56) References Cited

U.S. PATENT DOCUMENTS

| | | | | |
|---|---|---|---|---|
| 2,034,137 | A | * | 3/1936 | Dermot et al. ................ 401/266 |
| 2,600,426 | A | | 6/1952 | Paul |
| 2,755,968 | A | | 7/1956 | Fiant |
| 2,982,987 | A | | 5/1961 | Knapp |
| 3,602,601 | A | | 8/1971 | Zenger et al. |
| 3,644,707 | A | | 2/1972 | Costello |
| 3,710,985 | A | | 1/1973 | Baum |
| 3,774,231 | A | * | 11/1973 | Tullos ........................ 346/140.1 |
| 3,891,827 | A | | 6/1975 | Wyse |

(Continued)

FOREIGN PATENT DOCUMENTS

| | | |
|---|---|---|
| CN | 1331041 A | 1/2002 |
| CN | 1336150 A | 2/2002 |

(Continued)

OTHER PUBLICATIONS

"Part Number: CP Series, Description: application notes," V-Infinity, a division of CUI, Inc., Jan. 2009, pp. 1-8.

(Continued)

*Primary Examiner* — David Walczak
(74) *Attorney, Agent, or Firm* — Pepper Hamilton LLP (57) ABSTRACT

A dispenser includes a thermal storage tip and a housing having a reservoir for containing a product, such as a cosmetics product or a medicinal product. The thermal storage tip comprises a material that is capable of storing and retaining thermal energy during application of the product.

19 Claims, 7 Drawing Sheets

(56) References Cited

U.S. PATENT DOCUMENTS

| | | |
|---|---|---|
| 3,908,676 A | 9/1975 | Levine et al. |
| 4,029,422 A | 6/1977 | Pillsbury |
| 4,056,707 A | 11/1977 | Farnam |
| 4,182,497 A | 1/1980 | Ferreira et al. |
| 4,291,685 A | 9/1981 | Taelman |
| 4,465,073 A | 8/1984 | Schwob |
| 4,470,715 A | 9/1984 | Reuchlin et al. |
| 4,511,427 A | 4/1985 | Karliner et al. |
| 4,525,092 A * | 6/1985 | Shimizu et al. .............. 401/265 |
| 4,551,038 A * | 11/1985 | Baker et al. .................. 401/265 |
| 4,592,745 A | 6/1986 | Rex et al. |
| 4,602,741 A | 7/1986 | Faulkner, III et al. |
| 4,704,088 A | 11/1987 | Newman |
| 4,708,267 A | 11/1987 | Sieverding et al. |
| 4,874,117 A | 10/1989 | Kay et al. |
| 4,880,326 A | 11/1989 | Spivey et al. |
| 5,025,960 A | 6/1991 | Seager |
| 5,180,244 A | 1/1993 | Hirose |
| 5,316,196 A | 5/1994 | Reich |
| 5,531,763 A | 7/1996 | Mastri et al. |
| 5,626,472 A | 5/1997 | Pennetta |
| 5,816,728 A | 10/1998 | Nardolillo et al. |
| 5,951,185 A | 9/1999 | Kingsford et al. |
| 6,009,887 A | 1/2000 | Hertel |
| 6,027,272 A | 2/2000 | Spencer et al. |
| 6,102,518 A | 8/2000 | Taylor |
| 6,261,014 B1 | 7/2001 | Altobellis et al. |
| 6,402,411 B2 | 6/2002 | Spencer et al. |
| 6,565,523 B1 | 5/2003 | Gabourie |
| 6,669,389 B2 | 12/2003 | Gueret |
| 7,082,970 B2 | 8/2006 | Bartholomew et al. |
| 7,083,347 B2 | 8/2006 | Marcotte et al. |
| 7,147,395 B2 * | 12/2006 | Weiss et al. ................... 401/266 |
| 7,306,442 B2 | 12/2007 | Fox |
| 7,530,752 B2 | 5/2009 | Gueret |
| 7,959,369 B2 | 6/2011 | Gueret |
| 2002/0029859 A1 | 3/2002 | Weaver |
| 2002/0082625 A1 | 6/2002 | Huxel et al. |
| 2002/0121239 A1 | 9/2002 | Tonazzi et al. |
| 2002/0166631 A1 | 11/2002 | Dewitt |
| 2002/0185396 A1 | 12/2002 | Mainwaring et al. |
| 2003/0060925 A1 | 3/2003 | Bartholomew et al. |
| 2003/0129363 A1 | 7/2003 | Hoeft et al. |
| 2003/0171762 A1 | 9/2003 | Forchette et al. |
| 2004/0127952 A1 | 7/2004 | O'Phelan et al. |
| 2004/0190975 A1 | 9/2004 | Goodman et al. |
| 2004/0211789 A1 | 10/2004 | Osborn et al. |
| 2005/0175786 A1 | 8/2005 | Singh et al. |
| 2005/0197268 A1 | 9/2005 | Buskirk et al. |
| 2006/0039742 A1 | 2/2006 | Cable, Jr. et al. |
| 2006/0049203 A1 | 3/2006 | Boone et al. |
| 2006/0216104 A1 | 9/2006 | Bouix et al. |
| 2006/0216256 A1 | 9/2006 | Giniger et al. |
| 2007/0034224 A1 | 2/2007 | Dumler |
| 2007/0186951 A1 | 8/2007 | Gueret |
| 2009/0071499 A1 | 3/2009 | Wyatt et al. |
| 2011/0123252 A1 | 5/2011 | Thorpe |

FOREIGN PATENT DOCUMENTS

| | | |
|---|---|---|
| CN | 1355125 A | 6/2002 |
| CN | 1421362 A | 6/2003 |
| CN | 2606543 Y | 3/2004 |
| CN | 1499988 A | 5/2004 |
| CN | 200941885 Y | 9/2007 |
| EP | 0181184 A2 | 5/1986 |
| GB | 2262237 A | 6/1993 |
| JP | 06-064651 U | 9/1994 |
| JP | 8238884 A | 9/1996 |
| JP | 10-000001 U | 1/1998 |
| JP | 2000102583 | 4/2000 |
| JP | 2000279870 A | 10/2000 |
| JP | 2001000497 | 1/2001 |
| JP | 2002-035138 A | 2/2002 |
| JP | 2005211182 | 8/2005 |
| JP | 2005319300 A | 11/2005 |
| JP | 2006247037 | 9/2006 |
| JP | 2007-181668 A | 7/2007 |
| WO | 2005/058405 A1 | 6/2005 |

OTHER PUBLICATIONS

"Series: CP20, Description: 2.0 A Peltier Module," retrieved on Feb. 5, 2013, at <<http://www.cui.com/Product/Resource/PDF/CP20.pdf>>, CUI, Inc. May 7, 2012, pp. 1-5.

"Energizer L91 Ultimate Lithium," Product Datasheet, retrieved on Feb. 5, 2013, at <<http://data.energizer.com/PDFs/l91.pdf>>, Energizer Holdings, Inc., pp. 1-2.

"Frequently Asked Questions About Our Cooling and Heating Technology," retrieved on Feb. 5, 2013, at <<http://www.tellurex.com/technology/peltier-faq.php>>, Tellurex, 2009-2011, pp. 1-14.

Translated Japanese Office Action mailed Jan. 22, 2013 for Japanese patent application No. 2011-211113, a counterpart foreign application of US patent No. 7,883,287, 6 pages.

"Super simple PWM TEC controller," retrieved on Feb. 5, 2013, at <<http://redlum.xohp.pagesperso-orange.fr/electronics/simplePWM-TEC.html>>, Welcome to W's Laser-Projects page!, Vers. 1.0, Aug. 2010, pp. 1-3.

"Blistex—Lip Splash, Rolling Tip Applicator, Lip Moisturizer, SPF for Your Lips, Dermat . . . ," retrieved from the internet on May 10, 2007 at <<http://www.blistex.eu/whats_new.htm>>, 1 page.

Translated Chinese Office Action mailed Mar. 29, 2011 for Chinese Patent Application No. 200710188771.8, a counterpart foreign application of US Patent No. 7,883,287, 11 pages.

"Cosmogen Innovation in Progress," retrieved on Jun. 20, 2008, 1 page.

Translated Japanese Office Action mailed May 27, 2011 for Japanese Patent Application No. 2008-123531, a counterpart foreign application of US patent No. 7,883,287, 3 pages.

Translated Korean Office Action mailed Jun. 9, 2011 for Korean patent application No. 10/2008/43257, a counterpart foreign application of US patent No. 7,883,287, 5 pages.

Translated Korean Office Action mailed Sep. 29, 2011 for Korean patent application No. 10-2008-43257, a counterpart foreign application of U.S. Appl. No. 11/747,078, 6 pages.

Non-Final Office Action for US Appl. No. 13/022,193, mailed on May 21, 2012, Timothy Thorpe, "Dispenser With Thermal Storage Tip," 10 pages.

Chinese Search Report dated Sep. 30, 2013 for Chinese Patent Application No. 201110415705.6.

Notice of Rejection mailed Mar. 17, 2015 in corresponding Japanese Patent Application No. 2014-007958.

* cited by examiner

FIG. 7C

COSMETIC DEVICE WITH THERMAL STORAGE TIP

This application is a continuation of U.S. patent application Ser. No. 13/022,193, filed Feb. 7, 2011 (now U.S. Pat. No. 8,292,535), which is a continuation of U.S. patent application Ser. No. 11/747,078, filed May 10, 2007 (now U.S. Pat. No. 7,883,287), which are incorporated herein by reference in their entirety.

BACKGROUND

Devices exist for dispensing cosmetic or medicinal products. Such devices usually consist of an outer tubular shell or housing, a delivery mechanism for displacement of the cosmetic or medicinal products, and an applicator tip. For example, in the medical industry, applicators are employed for applying medicinal products, such as ointments, to portions of the body. In the cosmetics and personal care industries, applicators are used to apply lipstick, lip balm, skin creams, lotions, and other cosmetic products to portions of the body.

In many cases, these medicinal and cosmetic products may include skin care substances, such as aloe or lanolin, that provide a healing or therapeutic effect to heal damaged skin or maintain healthy skin. In addition, these products may include therapeutic substances, such as topical anesthetics, analgesics, fragrances, menthol, or other substances that provide a soothing or stimulating sensation when applied to skin of a user of the product. In addition to skin care substances, thermal treatments (e.g., application of heat and/or cold) are known to relieve pain, provide a therapeutic sensation, and to slow the body's natural response to injury so that a slower and more controlled healing process may ensue.

Existing cosmetic and medicinal dispensers are limited to application of products to the skin, and do not provide for thermal treatments of the skin. Accordingly, there remains a need in the art for improved dispensers.

SUMMARY

This summary is provided to introduce simplified concepts of dispensers with thermal storage applicator tips, which are further described below in the Detailed Description. This summary is not intended to identify essential features of the claimed subject matter, nor is it intended for use in determining the scope of the claimed subject matter.

This disclosure is directed to dispensers with thermal storage tips having relatively high thermal capacities, which are capable of storing and retaining thermal energy. The thermal storage tips may allow a product to be applied locally or topically to a selected area of a surface.

In some implementations, a housing may be coupled to the thermal storage tip and may have a reservoir for product storage. The thermal storage tip may have an application face for applying the product to the user's skin.

In some implementations, the thermal storage tip may comprise a material capable of storing and retaining thermal energy, such a metal, ceramic, composites, and/or other materials that can be heated or cooled and are able to retain the heated or cooled condition for a period of time.

In still further implementations, thermal storage tips may include an insert or liner. The insert may be positioned generally in the center of the tip and may include a product delivery passageway extending through the thermal storage tip for dispensing a product to the application face.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Overview

This disclosure is directed to dispensers with thermal storage tips that are able to store and maintain a level of thermal energy. Thermal storage tips may have an application face comprising various metals, ceramics, composites, and/or other materials that can be heated or cooled and are able to retain the heated or cooled condition for a period of time. A product may be dispensed from the dispenser through the thermal storage tip for application to a user's skin. By virtue of the thermal retention of the tip, thermal energy may be applied to the dispensed product so that it may be heated or cooled during application. Moreover, the application face of the thermal storage tip may transfer heat to or from the user's skin, thereby causing the user to feel a thermal sensation (warm or cool depending on the thermal energy in the thermal storage tip). In some cases, the heat transfer may also minimize or alleviate pain or discomfort caused by damage to the skin.

Illustrative Dispenser with Thermal Storage Tip

Figure 1:
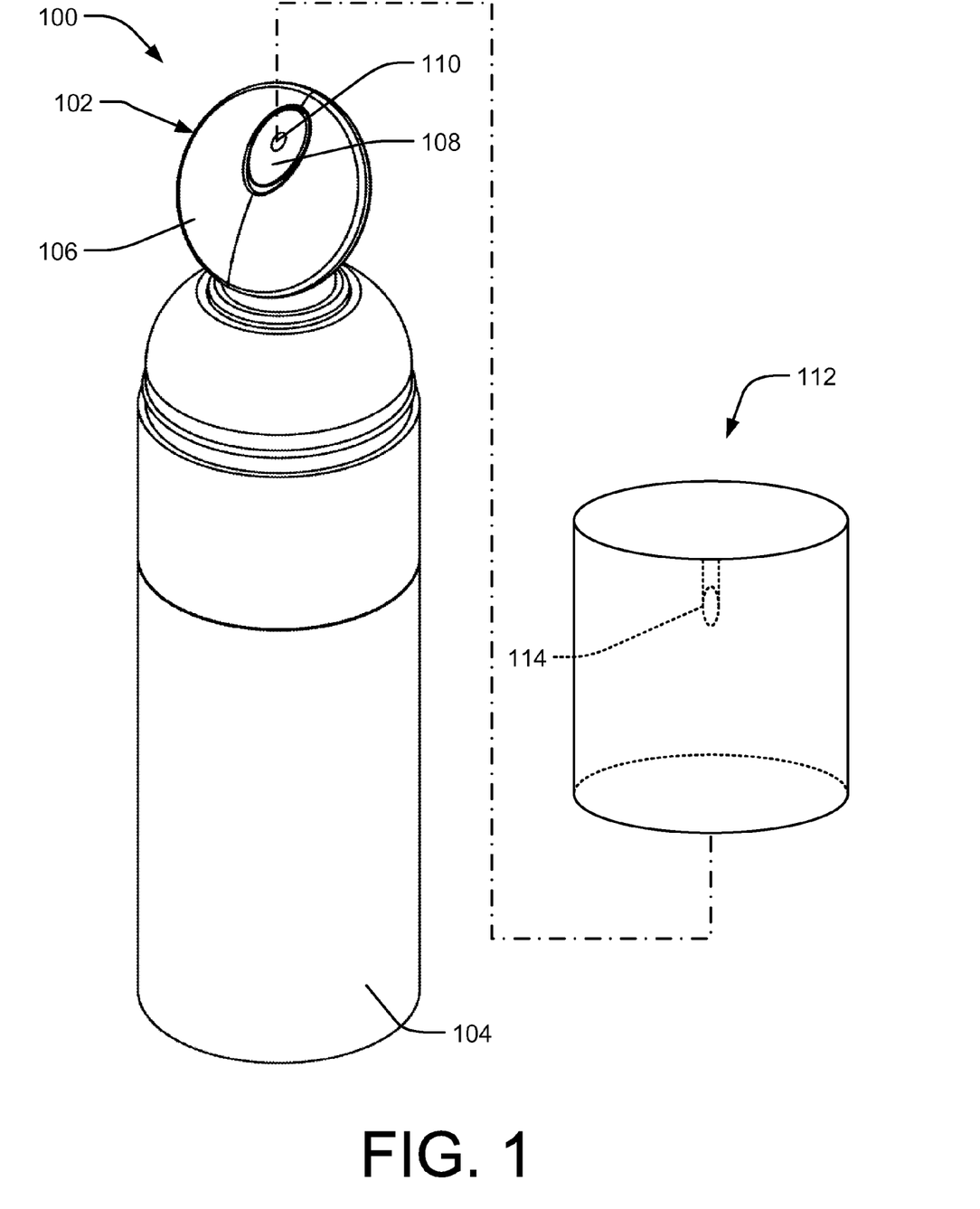
FIG. 1 is a perspective view of an illustrative dispenser with a thermal storage tip according to one implementation.

FIG. 1 represents an illustrative dispenser 100 with a thermal storage tip 102 and a housing 104. In this implementation, the thermal storage tip 102 comprises a generally disk-shaped applicator 106 made of a material capable of holding and retaining a thermal charge. In one implementation, the applicator 106 can be made of stainless steel. However, in other implementations, any suitable material may be used that is capable of retaining heat or cold during the application of the product. Examples of other suitable materials include, without limitation, metals (e.g., aluminum, titanium, steel, nickel, tin, copper, brass, alloys thereof, etc.), ceramics, high-density plastics, composites, or the like. In addition, in this implementation, the thermal storage tip includes a generally cylindrical insert 108 extending through the thermal storage tip 102 and forming a product delivery passageway 110 for the product in housing 104. The insert 108 may be made of a thermoplastic polymer, for example, which is non-reactive with the product stored in the reservoir 104. In other implementations, the insert 108 may be made of virtually any other material that is non-reactive or resistant to the product being dispensed, such as various metals, plastics, ceramics, composites, or the like.

The dispenser 100 also includes a cap 112 that encapsulates the thermal storage tip 102 when the dispenser is not in use and includes a plug 114 that seals the product delivery passageway 110. The plug 114 may be made of a thermoplastic polymer similar to insert 108 or any other material which is non-reactive or resistant to the product being dispensed, such as various metals, plastics, ceramics, composites, or the like. Additionally or alternatively, either the plug 114, the insert 108, or both may be elastomeric, such that when the cap is in place either the plug 114, insert 108, or both, may expand and deform somewhat to seal the product delivery passageway 110.

Figure 2:
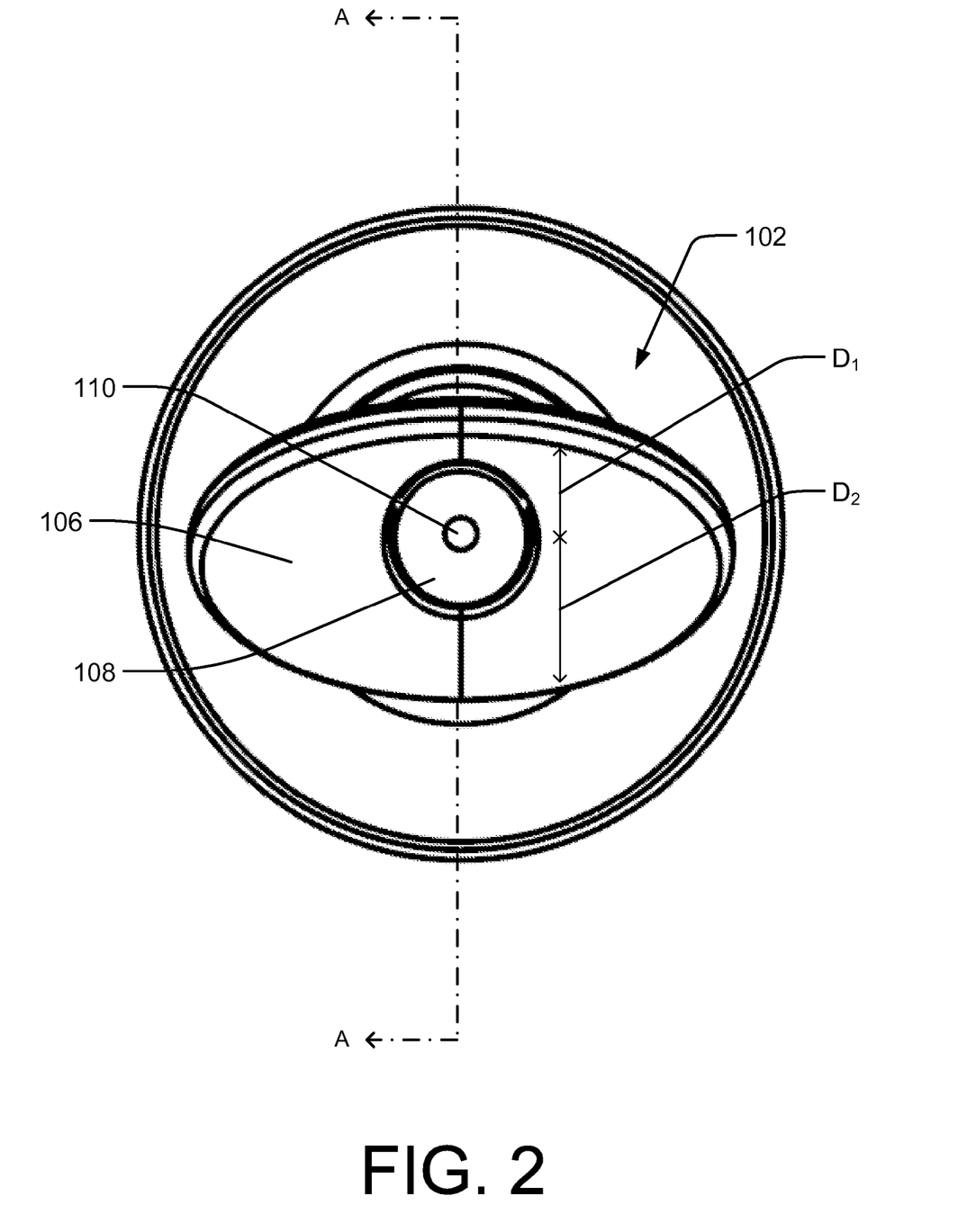
FIG. 2 is a top view of the thermal storage tip of the dispenser of FIG. 1.

FIG. 2 is a top view of the thermal storage tip of dispenser 100 in more detail. Again, the thermal storage tip 102 generally comprises the application face 106, the insert 108, and the product delivery passageway 110, which forms a dispensing path for the product in housing 104. In one implementation, the product delivery passageway 110 is positioned slightly off center within insert 108. This is illustrated by the dimension lines $D_1$ and $D_2$ in FIG. 2, where $D_1$ is the distance from the topmost point of thermal storage tip 102 to the center of the product delivery passageway 110, and $D_2$ is the distance from the bottommost point of thermal storage tip 102 to the center of the product delivery passageway 100. As shown in the FIG. 2, $D_2$ is greater than $D_1$.

In this implementation the thermal storage tip is shown as being a generally disk-shaped body. In addition, the thermal storage tip 102 in this implementation is made at least in part of stainless steel, and has a mass of between about 300 and about 700 milligrams, and a volume of between about 300 and about 700 millimeters$^3$. More specifically, the thermal storage tip 102 has a mass of about 500 milligrams and a volume of about 500 millimeters$^3$. In some implementations, the thermal storage tip may have a mass of at least about 300 milligrams (0.3 grams) and at most about 600 milligrams (0.6 grams), and a volume of at least about 450 millimeters$^3$ and at most about 550 millimeters$^3$. Further, in some implementations, the application face 106 may have a surface finish of between about 32 and about 64 micro-inches, while in other implementations the application face 106 may have a surface finish of about 30 to about 70 micro-inches. The surface finish corresponds to the measurements of the small scale variations in the height of the physical surface. A surface finish of about 64 micro-inches may be accomplished by casting and buffing inside the fabrication mold, while finer surface finishes may be achieved using one or more secondary operations, such as buffing, polishing, or chroming, for example. While features of various illustrative implementations are described, in other implementations, the storage tip may be configured in any form suitable for the application of the product contained in dispenser 100. For example, the thermal storage tip may be constructed in any other suitable shape and size and may have any suitable mass, surface finish, and/or surface treatment desired for a given application.

Figure 3:
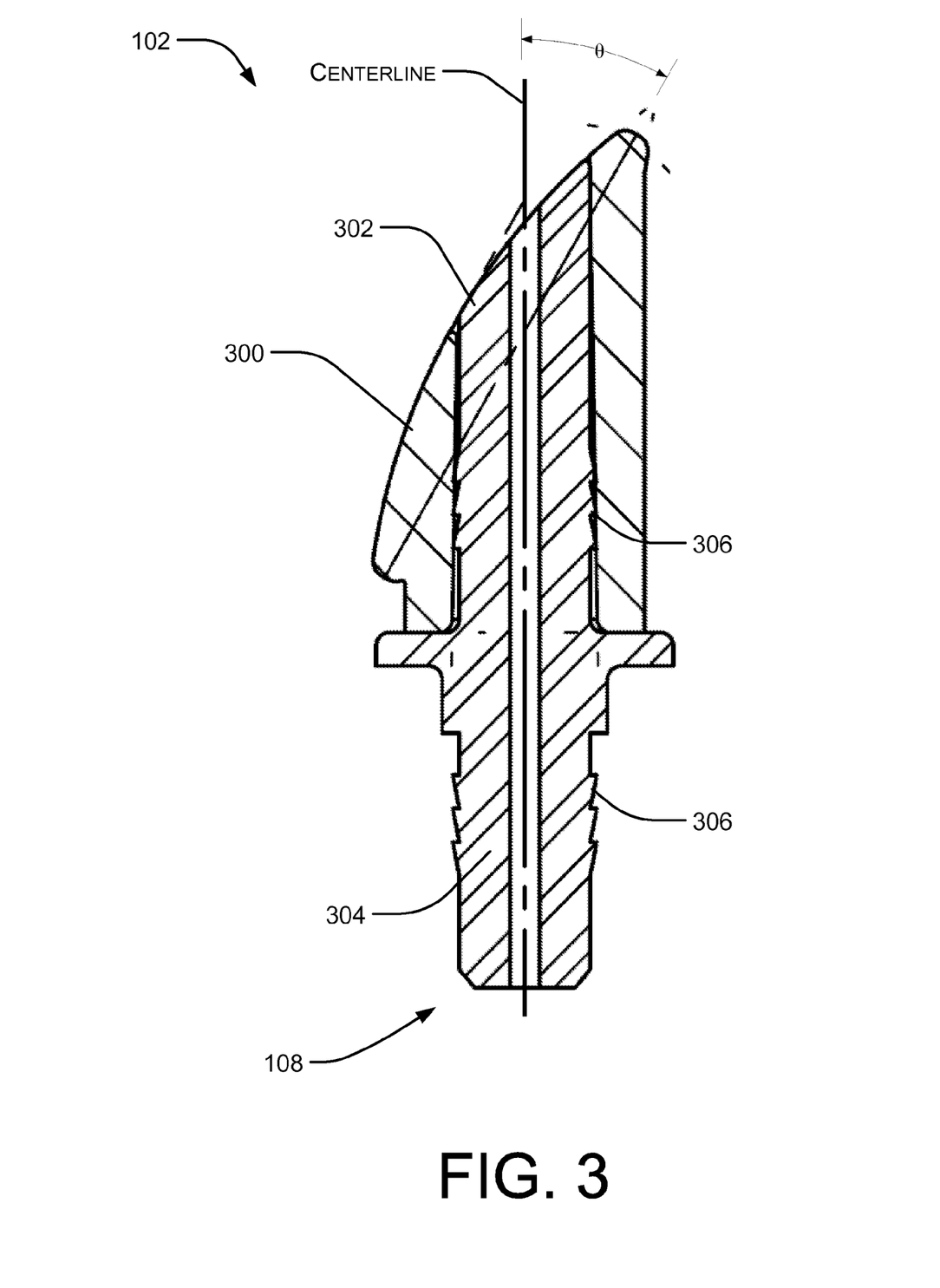
FIG. 3 is a cross-sectional view of the thermal storage tip of the dispenser shown in FIG. 1, taken along line A-A of FIG. 2.

FIG. 3 shows an angle θ of the application face with respect to a centerline of the thermal storage tip. In the illustrated implementation, the angle θ is about 60°. This design facilitates application of the product to the user's skin. However, other designs may be used. For example, in other implementations the angle θ may be between about 30° and about 75°. Still further implementations may have angles anywhere from 0° to 90°.

FIG. 3 also illustrates the construction of the thermal storage tip 102. As discussed above, the thermal storage tip 102 includes a body 300 made of material capable of retaining thermal energy and an insert 108. The insert 108 includes a neck portion 302, which extends through a bore in the body 300, and a connector stem 304 usable to retain the thermal storage tip 102 in the housing 104. The insert 108 and may be secured to the body 300 and/or the housing 104 by, for example, a press-fit, snap-fit, adhesive, and/or engagement by one or more engagement features. In this way the thermal storage tip 102 may be fixed to the housing 104 against movement relative to the housing 104. In the illustrated implementation, the insert is retained in both the body 300 of the thermal storage tip and the housing 104 by a series of barbs 306. In some implementations, the insert 108 comprises polypropylene or another thermoplastic polymer.

Figure 4:
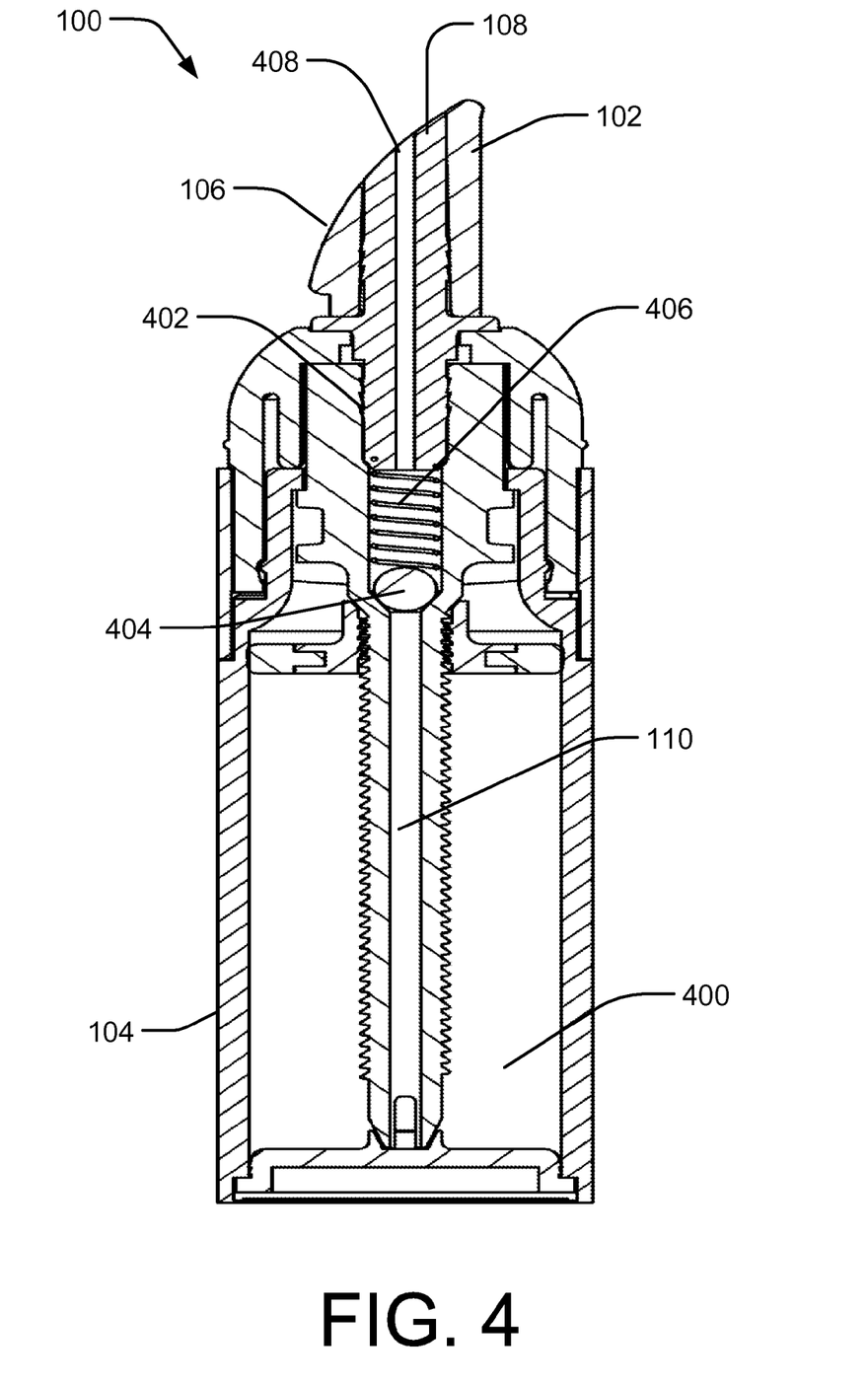
FIG. 4 is a cross-sectional view of the dispenser shown in FIG. 1, taken along line A-A of FIG. 2.

FIG. 4 is a cross-sectional view of dispenser 100, showing details of the housing 104. As shown in FIG. 4, the dispenser 100 has a reservoir 400. The product delivery passageway 110 extends from the reservoir 400, through the thermal storage tip 102, and terminates in an opening 408 on the application face 106. In the illustrated implementation, the product is transported through the product delivery passageway 110 by rotating the housing 104 such that the product is dispensed through the thermal storage tip 102 by way of a check valve comprised of a ball 404 and a spring 406. However, in other implementations, any suitable delivery mechanism may be used.

The following is a discussion of examples, without limitation, of delivery mechanisms for dispensing a product. The first example may be implemented using a click or a reverse click operation, whereby the user may operate the dispenser by moving the applicator member relative to the housing member in either a clockwise or counterclockwise direction.

Another example delivery mechanism for dispensing the product may be a squeeze operation. In certain embodiments wherein the delivery mechanism is a squeeze operation, when pressure is applied to the housing containing the reservoir, the product in the reservoir may be forced, by the squeezing action, through the dispenser via a product delivery passageway for application to the user's skin.

In yet another example, a delivery mechanism for dispensing the product may be by a pressurized dispenser, such as an aerosol dispenser. In certain embodiments wherein the delivery mechanism is an aerosol delivery mechanism, the composition will be held under pressure in a container and will be dispersed along with an aerosol propellant in response to actuation by a user. Actuation may be by depressing, rotating, tilting, or otherwise manipulating the thermal storage tip, pressing a button, and/or by any other suitable dispensing mechanism. Details of the construction and propellant of an aerosol dispenser are within the skill of one of ordinary skill in the art and will, therefore, not be described in detail herein.

In yet another example, a delivery mechanism for dispensing product may be an airless pump. The term airless pump refers to a pump that provides dispensing of a substance from a container under pressure in essentially a single direction without permitting reverse (intake) flow of air via the pump. That is, as product is pumped from the container, the pumped product is not replaced with a corresponding volume of air through the pump. In addition to preventing reverse intake flow of air, an airless pump typically does not allow intake of any other substances to replace the volume of product pumped out of the container. For example, an airless pump could include a one-way valve, such as a check valve.

Further illustrated in FIG. 4, the thermal storage tip 102 is coupled to housing 104 by barbs located on a connector stem 402 of the thermal storage tip, which engage an interior of the housing 104. However, in other implementations the housing may be coupled to the thermal storage tip through any suitable means. Fabrication of housing 104 and thermal storage tip 102 may be accomplished through a separate manufacturing process, a co-molding process, or any other suitable production process.

Illustrative Unitary Thermal Storage Tip

While the dispenser with a thermal storage tip 100 shown in FIGS. 1-4 includes an insert 108, in other implementations the insert may be formed integrally with the body of the thermal storage tip, may be truncated, or omitted entirely. For example, where the product to be dispensed is not corrosive or otherwise reactive with the thermal storage tip (or for any other desired reason), the insert may be formed integrally with and of the same material as the thermal storage tip. In that case, the thermal storage tip may consist of a unitary body with a dispensing path formed through the unitary body itself.

Figure 5:
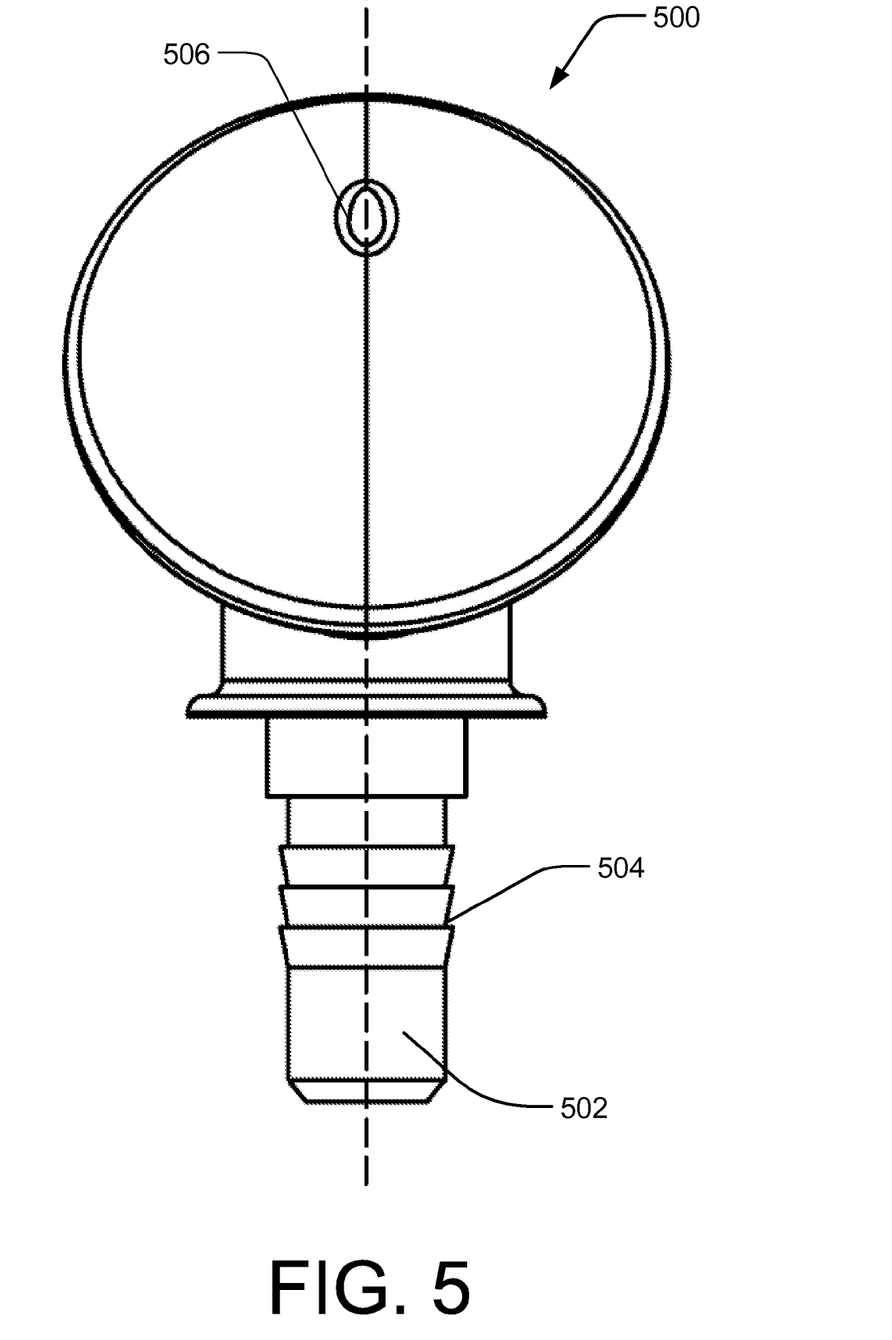
FIG. 5 is a front view of a thermal storage tip according to another illustrative implementation, in which the thermal storage tip is unitary.

FIG. 5 shows an illustrative implementation in which a thermal storage tip 500 consists of a unitary body made of material capable of storing thermal energy. In this implementation, the thermal storage tip 500 includes a stem 502 with a series of barbs 504 configured to secure the tip 500 in a housing of a dispenser. A dispensing passageway 506 is formed through the interior of the thermal storage tip 500 to convey the product to be dispensed. In other respects, the thermal storage tip 500 is the same or similar to that shown in FIGS. 1-4. Accordingly, additional details of the applicator tip have been omitted for brevity.

Illustrative Thermal Storage Tip with Thermal Storage Applicator

Figures 6A, 6B:
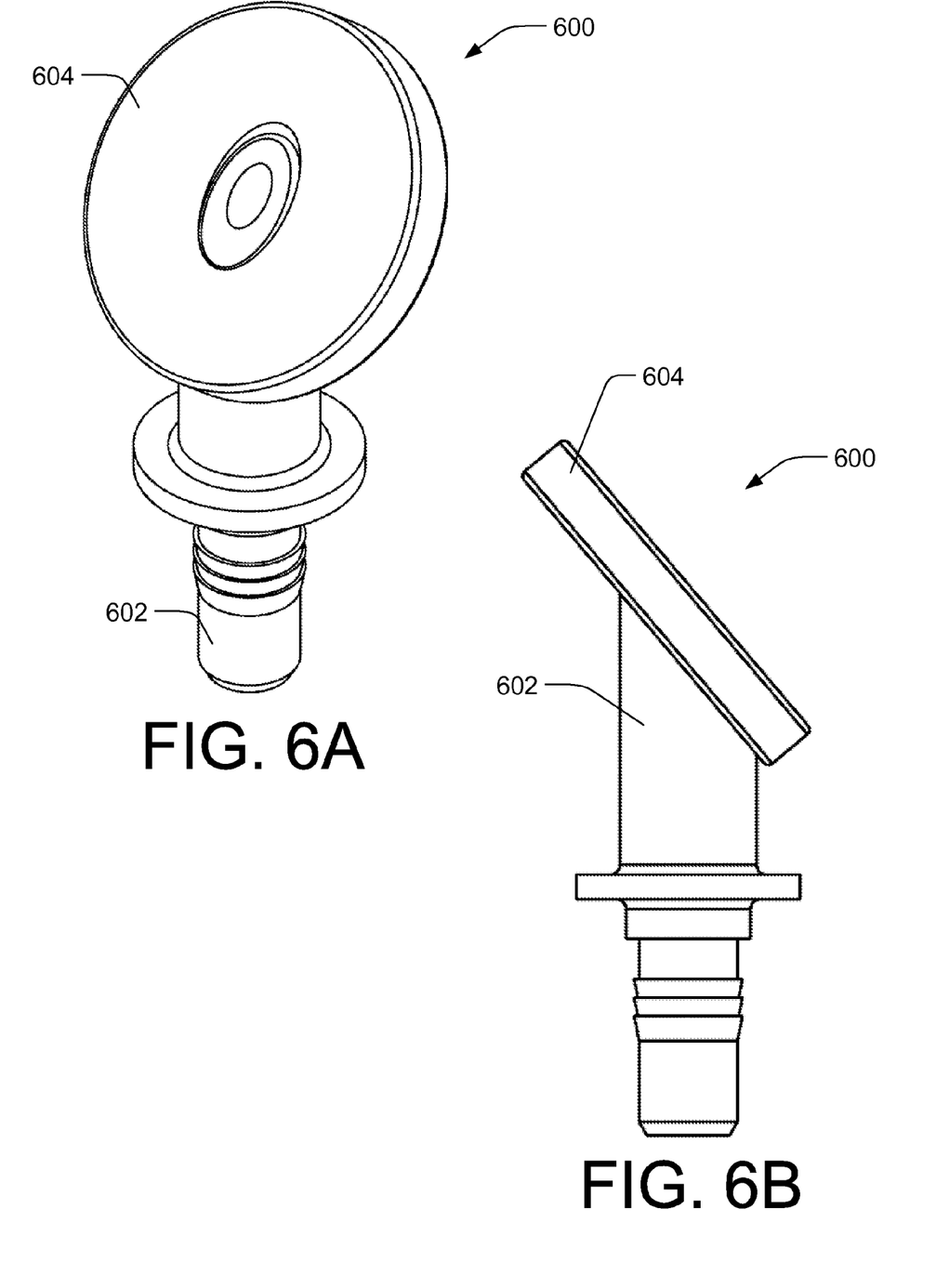
FIGS. 6A and 6B are perspective and side views, respectively, of a thermal storage tip according to another illustrative implementation, in which the thermal storage tip includes a thermal storage applicator.

FIGS. 6A and 6B illustrate a thermal storage tip 600 according to yet another illustrative implementation. In this implementation, the thermal storage tip 600 comprises a body 602 constituting a majority of the thermal storage tip, and an applicator 604 coupled to the body 602. The applicator 604 comprises a relatively thin member made of thermal-storage material. In the applicator 604 is illustrated as being generally disk- or ring-shaped. However, in other implementations, the applicator 604 may comprise a relatively thin cap or cover that is sized and shaped to fit over the top of the body 602. In practice, the body 602 and applicator 604 may be configured in virtually any desired shape, such as disk-shaped, oval, elliptical, spherical, curvilinear, trapezoidal, or the like. In various implementations, the applicator 604 may be coupled to the body 602 by adhesive, press fit, snap fit, one or more ribs or barbs, or any other suitable fastening means.

The body 602 of the thermal storage tip 600 may be made of a thermoplastic polymer, for example, which is relatively light weight and inexpensive. In other implementations, the body 602 may be made of virtually any other desired material, such as various metals, plastics, ceramics, composites, or the like. In one implementation, the applicator 604 can be made of stainless steel. However, in other implementations, any suitable material may be used that is capable of retaining heat or cold during the application of the product. Examples of other suitable materials include, without limitation, metals (e.g., aluminum, titanium, steel, nickel, tin, copper, brass, alloys thereof, etc.), ceramics, high-density plastics, composites, or the like.

Alternative Illustrative Dispenser with a Thermal Storage Tip

In the implementations shown in FIGS. 1-6, the thermal storage tip 102 is shown as having a generally convex (FIGS. 1-5) or flat (FIGS. 6A and 6B) disk-shaped body. However, in other implementations, thermal storage tips may take any other desired form, such as generally spherical, cylindrical, planar, elliptical, curvilinear, parabolic, flat, trapezoidal, combinations of the foregoing, or the like.

Figure 7A:
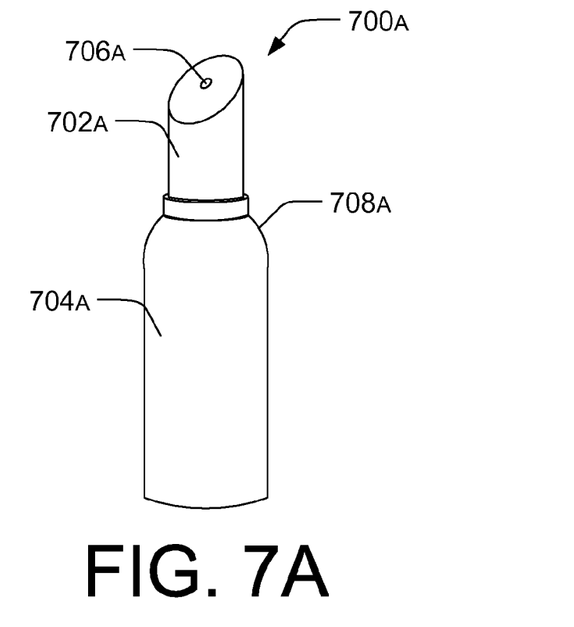
FIGS. 7A-7C are perspective views of three other dispensers with thermal storage tips, according to other illustrative implementations.
Figure 7B:
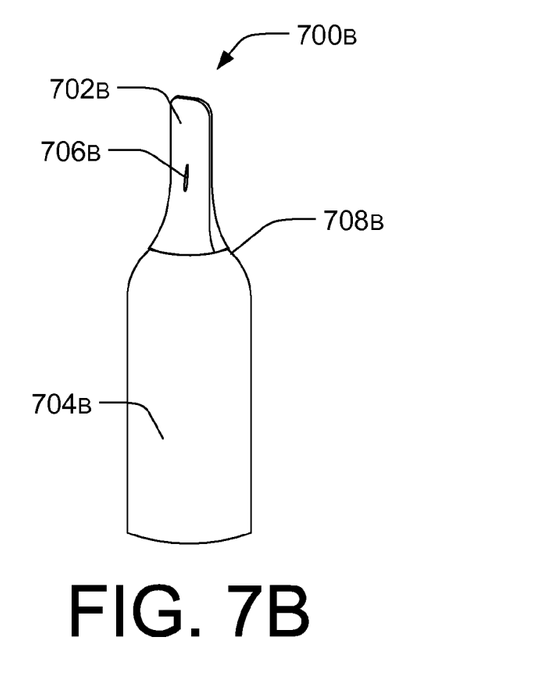
Figure 7C:
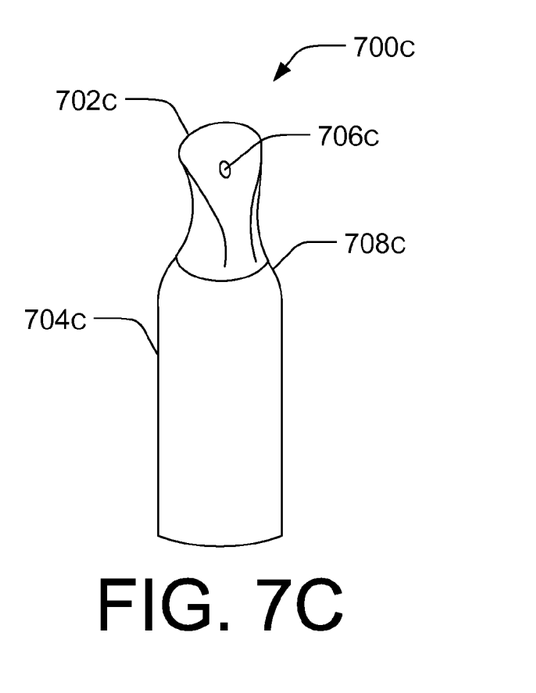

FIG. 7A-7C show several alternative dispensers 700a-700c with various configurations and shapes of thermal storage tips. The dispensers 700a-700c shown in these implementations each include a thermal storage tip 702a-702c and a housing 704a-704c with a reservoir. In particular, the housings 704a-704c shown in these implementations are flexible tubes that may be squeezed to dispense product from a dispensing path 706a-706c through the thermal storage tip 702a-702c.

The thermal storage tips 702a-702c may be coupled to the respective housings 704a-704c by placing them over a narrowed neck 708a-708c of the housing and attaching them to the housing 704a-704c by, for example, crimping, adhesive, press-fit, snap-fit, retaining ribs or barbs on the inside of the thermal storage tip and/or the outside of the narrowed neck of the housing, and/or by any other suitable attachment means.

In still other implementations, dispensers may additionally or alternatively include a brush, a sponge, or various other features to assist in the application of a dispensed product to a user's skin.

While the dispensers with thermal storage tips shown in FIGS. 1-7 are comprised of a separate applicator tip and housing, in other implementations to decrease manufacturing costs, or for any other desired reason, the applicator tip and some or all of the housing may be formed integrally.

CONCLUSION

Although the invention has been described in language specific to structural features and/or methodological acts, it is to be understood that the invention is not necessarily limited to the specific features or acts described. Rather, the specific features and acts are disclosed as illustrative forms of implementing the invention.

What is claimed is:

1. A dispenser comprising:
a housing having a reservoir for containing a product;
a thermal storage tip coupled to the housing, the thermal storage tip comprising a metal or a ceramic and a generally convex, disk-shaped body and having an application face for applying the product to a surface; and
an insert disposed in the thermal storage tip, the insert defining a product delivery passageway in communication with the reservoir, the insert being truncated relative to the application surface of the thermal storage tip, the product delivery passageway extending through the thermal storage tip and terminating in an aperture in the application face;
wherein the thermal storage tip is fixed to the housing against movement relative to the housing.

2. The dispenser of claim 1, wherein the thermal storage tip comprises stainless steel.

3. The dispenser of claim 1, wherein the thermal storage tip comprises a generally curvilinear shape, a generally cylindrical shape, or a generally planar shape.

4. The dispenser of claim 1, wherein the thermal storage tip has a mass of at least about 0.3 grams and at most about 0.6 grams.

5. The dispenser of claim 1, wherein the thermal storage tip has a volume of at least about 300 millimeters$^3$ and at most about 700 millimeters$^3$.

6. The dispenser of claim 1, wherein the insert comprises polypropylene.

7. The dispenser of claim 1, wherein the insert comprises a thermoplastic polymer.

8. The dispenser of claim 1, further comprising a product delivery mechanism to dispense product from the dispenser, the product delivery mechanism comprising:
- a reverse click motion delivery mechanism;
- a click motion delivery mechanism;
- a squeeze tube delivery mechanism;
- an airless pump delivery mechanism; or
- an aerosol delivery mechanism.

9. The dispenser of claim 1, wherein the thermal storage tip comprises aluminum.

10. A device for applying a cosmetic product, the device comprising:
- a housing having a reservoir for containing a product;
- a thermal storage tip comprising a metal or a ceramic and a generally convex, disk-shaped body and having an application face for applying the product to a surface, wherein the application face defines an aperture and the thermal storage tip defines an internal passageway for communicating product from the housing to an aperture at the application face; and
- wherein the thermal storage tip is fixed to the housing against movement relative to the housing.

11. The device of claim 10, further comprising an insert attached at one end to the housing and extending into the internal passageway and together defining a product passageway for communicating product from the housing to an aperture in the application face.

12. The device of claim 11, wherein insert extends into and occupies substantially the entire length of the internal passageway defined by the thermal storage tip.

13. The device of claim 11, wherein the insert extends partially into the internal passageway defined by the thermal storage tip.

14. The device of claim 10, wherein the thermal storage tip is coupled to the housing.

15. The device of claim 10, wherein the thermal storage tip has a volume of at least about 450 millimeters$^3$ and at most about 550 millimeters$^3$.

16. The device of claim 10, further comprising a product delivery mechanism to dispense product from the device, the product delivery mechanism comprising:
- a reverse click motion delivery mechanism;
- a click motion delivery mechanism;
- a squeeze tube delivery mechanism;
- an airless pump delivery mechanism; or
- an aerosol delivery mechanism.

17. A device for applying a cosmetic product, the device comprising:
- a housing having a reservoir for containing a product;
- a thermal storage tip comprising a metal or a ceramic and having an application face for applying the product to a surface, wherein the application face defines an aperture and the thermal storage tip defines an internal passageway for communicating product from the housing to an aperture at the application face; and wherein the thermal storage tip is fixed to the housing against movement relative to the housing; and
- an insert attached at one end to the housing and extending into the internal passageway and together defining a product passageway for communicating product from the housing to an aperture in the application face, wherein the insert extends partially into the internal passageway defined by the thermal storage tip.

18. The device of claim 17, wherein the thermal storage tip comprises a generally convex, disk-shaped body.

19. The device of claim 17, wherein the thermal storage tip comprises a generally curvilinear shape, a generally cylindrical shape, or a generally planar shape.

* * * * *